(12) United States Patent
Merz

(10) Patent No.: US 9,776,692 B2
(45) Date of Patent: Oct. 3, 2017

(54) SINGLE-PLATFORM INTEGRATED AQUATIC SPECIES AND HABITAT SAMPLING SYSTEM

(71) Applicant: S. P. Cramer & Associates, Gresham, OR (US)

(72) Inventor: Joseph Merz, Los Gatos, CA (US)

(73) Assignee: S.P. Cramer & Associates, Inc., Gresham, OR (US)

( * ) Notice: Subject to any disclaimer, the term of this patent is extended or adjusted under 35 U.S.C. 154(b) by 62 days.

(21) Appl. No.: 14/789,890

(22) Filed: Jul. 1, 2015

(65) Prior Publication Data

US 2016/0003713 A1   Jan. 7, 2016

Related U.S. Application Data

(60) Provisional application No. 62/020,278, filed on Jul. 2, 2014.

(51) Int. Cl.
*G01N 1/20* (2006.01)
*B63B 35/34* (2006.01)
(Continued)

(52) U.S. Cl.
CPC .............. *B63B 35/34* (2013.01); *B63B 35/00* (2013.01); *G01N 1/12* (2013.01); *G01N 33/18* (2013.01);
(Continued)

(58) Field of Classification Search
None
See application file for complete search history.

(56) References Cited

U.S. PATENT DOCUMENTS 254,022 A   2/1882  Jones
359,311 A   3/1887  Bateman
(Continued)

FOREIGN PATENT DOCUMENTS

WO   2011029958 A1   3/2011

OTHER PUBLICATIONS

Miller, J.M., 1973 A quantitative push-net system for transect studies of larval fish and macrozooplankton. Limnol.Oceanogr., 18:175-8.*

(Continued)

*Primary Examiner* — Paul West
*Assistant Examiner* — Mark A Shabman
(74) *Attorney, Agent, or Firm* — Santangelo Law Offices, PC

(57) ABSTRACT

Low or no disturbance sampling can be accomplished such as through a single-platform aquatic species and habitat sampling system with data integration and rapid processing capabilities that can address the need for sampling at variable depths over varied habitats, along with the simultaneous collection of linked physical and biological data. The platform may be based on a 24-36 foot boat, and may include a net mouth opener brace for an adjustable concentrator net and smaller drift net which may be attached to an adjustable sample chamber, perhaps containing variable mesh capture nets as well as cameras, water sampling equipment, and water quality sensors integrated with a fish finder, GPS, and other monitoring and data recording equipment. The depth of the net mouth opener brace and sample chamber may be adjustable using a depth control.

13 Claims, 3 Drawing Sheets

(51) Int. Cl.
  *B63B 35/00* (2006.01)
  *G01N 1/12* (2006.01)
  *G01N 33/18* (2006.01)
  *G01N 1/10* (2006.01)
  *G01N 1/40* (2006.01)

(52) U.S. Cl.
  CPC ............... *G01N 2001/1025* (2013.01); *G01N 2001/1093* (2013.01); *G01N 2001/4088* (2013.01)

(56) References Cited

U.S. PATENT DOCUMENTS

| | | |
|---|---|---|
| 404,132 A | 5/1889 | Travis |
| 1,561,653 A | 11/1925 | Linguist |
| 1,719,591 A | 7/1929 | Collins |
| 2,253,688 A | 8/1941 | Collins |
| 2,323,318 A | 7/1943 | Farkas |
| 2,564,598 A | 8/1951 | Grimshaw et al. |
| 2,651,874 A | 9/1953 | Key |
| 2,726,471 A | 12/1955 | Uus |
| 2,765,577 A | 10/1956 | Scruggs |
| 2,794,191 A | 6/1957 | Gaskouitz |
| 2,834,138 A | 5/1958 | Pedersen |
| 3,078,617 A | 2/1963 | Dempsey |
| 3,085,534 A | 4/1963 | Rabinow et al. |
| 3,087,338 A | 4/1963 | Horbinski et al. |
| 3,148,476 A | 9/1964 | Ethridge |
| 3,196,576 A | 7/1965 | Thomas, Sr. |
| 3,246,419 A | 4/1966 | Pawelka |
| 3,268,081 A | 8/1966 | Menkee et al. |
| 3,304,645 A | 2/1967 | Hardesty et al. |
| 3,342,032 A | 9/1967 | Cox et al. |
| 3,462,858 A | 8/1969 | Francklyn |
| 3,555,721 A | 1/1971 | Furuoka |
| 3,673,976 A | 7/1972 | Reynolds |
| 3,704,784 A | 12/1972 | Craggs et al. |
| 3,730,119 A | 5/1973 | Budris et al. |
| 3,791,327 A | 2/1974 | Deveney |
| 3,793,761 A | 2/1974 | Bonham |
| 3,804,177 A | 4/1974 | Renfroe |
| 3,871,332 A | 3/1975 | Hayashi |
| 3,902,457 A | 9/1975 | Musgrove et al. |
| 3,933,113 A | 1/1976 | Dornak et al. |
| 3,942,457 A | 3/1976 | Keyes et al. |
| 3,966,613 A | 6/1976 | Kirk et al. |
| 3,967,585 A | 7/1976 | Monaco |
| 4,020,777 A | 5/1977 | Brown et al. |
| 4,045,907 A | 9/1977 | Mumford |
| 4,141,308 A | 2/1979 | Gainey |
| 4,214,544 A | 7/1980 | Dashew et al. |
| 4,224,755 A * | 9/1980 | Bourret ................. A01K 73/02 43/9.1 |
| 4,292,758 A | 10/1981 | Kuna et al. |
| 4,349,985 A | 9/1982 | Kodaka |
| 4,351,438 A | 9/1982 | Morton |
| 4,399,629 A | 8/1983 | Duncan |
| 4,434,572 A | 3/1984 | Sheldon et al. |
| 4,455,960 A | 6/1984 | Aker |
| 4,483,440 A | 11/1984 | Ware |
| 4,514,924 A * | 5/1985 | Ojserkis ................. A01K 73/04 43/9.1 |
| 4,627,189 A | 12/1986 | Pippin et al. |
| 4,642,934 A | 2/1987 | Carlson et al. |
| 4,676,893 A | 6/1987 | Travade et al. |
| 4,807,552 A | 2/1989 | Fowler |
| 4,826,465 A | 5/1989 | Fleischmann |
| 4,919,637 A | 4/1990 | Fleischmann |
| 4,955,843 A | 9/1990 | Bolanos et al. |
| 5,097,795 A | 3/1992 | Adey |
| 5,117,774 A | 6/1992 | English et al. |
| 5,123,195 A * | 6/1992 | Hawkins ................. A01K 61/90 43/9.2 |
| 5,154,016 A | 10/1992 | Fedora et al. |
| 5,165,193 A | 11/1992 | Dankwardt |
| 5,173,182 A | 12/1992 | Debellian |
| 5,181,479 A | 1/1993 | Hiebert |
| 5,203,732 A | 4/1993 | Cusson |
| 5,222,458 A * | 6/1993 | Pippy ..................... A01K 61/90 119/247 |
| 5,282,763 A | 2/1994 | Dixon |
| 5,309,664 A | 5/1994 | Wright |
| 5,363,587 A | 11/1994 | Nordling |
| 5,574,232 A | 11/1996 | Davidson et al. |
| 5,631,530 A | 5/1997 | Hoppe et al. |
| 5,713,293 A | 2/1998 | Shiffler et al. |
| 5,806,232 A | 9/1998 | James |
| 5,947,788 A | 9/1999 | Derrah |
| 6,041,537 A | 3/2000 | Sullivan |
| 6,115,681 A | 9/2000 | Foreman et al. |
| 6,187,530 B1 | 2/2001 | Scholin et al. |
| 6,568,341 B1 | 5/2003 | Sosa |
| 7,225,102 B2 | 5/2007 | Stiner et al. |
| 7,467,062 B2 | 12/2008 | Stiner et al. |
| 7,669,360 B2 | 3/2010 | Davidson |
| 7,846,315 B2 | 12/2010 | Amirkhanian |
| 8,101,069 B2 | 1/2012 | Martin |
| 8,244,941 B2 | 8/2012 | Robertson et al. |
| 8,286,513 B2 | 10/2012 | Lange |
| 8,366,943 B2 | 2/2013 | Jarvinen |
| 8,718,939 B2 | 5/2014 | Hamann et al. |
| 9,021,971 B2 | 5/2015 | Escher |
| 2002/0198679 A1 | 12/2002 | Victor et al. |
| 2008/0223278 A1 | 9/2008 | Carro Donna et al. |
| 2009/0171901 A1 | 7/2009 | Bathiche et al. |
| 2010/0005857 A1 | 1/2010 | Zhang et al. |
| 2013/0283670 A1 | 10/2013 | Parys et al. |

OTHER PUBLICATIONS

Guidelines for Sampling Fish in Inland Waters. Food and Agriculture Organization of the United Nations. Welcomme, Robin L. ed. 1980.*

Herke, William H. A Boat-Mounted Surface Push-Trawl for Sampling Juveniles in Tidal Marshes. Louisianna State University, Baton Rouge, LA. Bureau of Sport Fisheries and Wildlife. The Progressive Fish-Columnist. Date unknown. 3 pages.

* cited by examiner

SINGLE-PLATFORM INTEGRATED AQUATIC SPECIES AND HABITAT SAMPLING SYSTEM

BACKGROUND

The present invention relates generally to the field of environmentally sensitive monitoring of aquatic species and habitats. The weaknesses of current monitoring methods used to determine status and trends in fish populations have been known for many years. Currently, monitoring techniques such as trawls, tow nets, and beach seines are used. However, these techniques are generally habitat-specific and of limited range, among other aspects. Trawls and tow nets can sample relatively large areas but are only effective in deep channels and cannot be used in backwaters or shallows, whereas seines can only sample relatively small areas in shallow water and cannot be used effectively in deeper, open water. For instance, the system described in U.S. Pat. No. 6,568,341 is not adequately applicable to deep water sampling. The system described in U.S. Pat. No. 6,306,350 does not adequately address the sample collection needs or the variability needed. The system described in U.S. Pat. No. 5,722,196 is not adequately applicable to deep or open water sampling. The system described in U.S. Pat. No. 8,286,513 is not adequately applicable to the sampling of larger aquatic species. The system described in U.S. Pat. No. 4,554,826 is not adequately applicable to the sampling of varied species. The system described in U.S. Pat. No. 4,446,749 is not adequately applicable to the sampling of varied species and may not be appropriate for the desired sampling in shallower water.

Perhaps one of the most significant problems that scientists and managers have faced is the efficient monitoring of fish populations in estuarine areas. Current monitoring in these areas relies almost exclusively on trawls employed in relatively large, deep channels. These trawls are known to have poor or unknown efficiency and are difficult to relate to habitat conditions important to pelagic fishes. Since trawls are not suited to the sampling of shoals, shallows, inter-tidal, or sub-tidal habitats—which are increasingly recognized as critical habitat for many sensitive estuarine species—beach seining is often used to sample in these areas. However, this method requires shore access and smooth, sparsely vegetated substrates, which can limit the areas in which it can be employed.

At least four additional problems have presented themselves from the perspective of scientists and managers. First, current methods of sampling have limited effectiveness in sampling larval species or other small organisms such as zooplankton and phytoplankton.

A second problem is that current techniques suffer from a lack of data integration. For example, biological sampling using current techniques is often done by passing a net through the water to collect, identify, and catalog fish and other aquatic organisms, and then placing water quality sensors in the water, waiting for them to acclimate, and then taking a reading. This process precludes the simultaneous collection of organisms and data regarding the environment from which they are collected. Further, the employment of multiple sampling methods (e.g., trawls for deep water, seines for shallow water), each over limited geographic areas and each with different efficiencies, makes it difficult to reliably estimate basic metrics such as population size and structure.

A third problem is that current monitoring techniques are costly and time consuming. For example, trawls typically involve towing nets which direct fish and other aquatic organisms into a collection device which must be recovered to identify and enumerate organisms such as fish and invertebrates—a process which requires extended periods of sampling downtime.

A fourth problem is that current methods of sampling often cause excessive injury or mortality of ESA-listed fish or other sensitive species, which can become trapped or entangled by the nets.

In addition to the four specific issues described above, a wide variety of other problems exist in the field as it stands. These include, but are not limited to, sample accuracy, cost of materials, cost of labor, repairs, and environmental degradation, among others.

SUMMARY OF THE INVENTION

The present invention overcomes the problems of prior systems and can incorporate elements such as: a concentrator net 100 and smaller drift net 102 which can allow for the simultaneous collection of larval species, zooplankton, and phytoplankton as well as larger fish and aquatic organisms; one or more sensors 106 which can record physical habitat data (e.g., depth, turbidity, temperature, dissolved oxygen, conductivity, phytoplankton level, nutrient concentration, total suspended solids, chlorophyll levels) or mapping data and may associate this data with sampling events; and an accessible sample chamber 108, perhaps a live well or live box, which can allow for dip netting, and may have one or more capture net slots or screens which can be pulled individually for rapid sampling, and which also can have a flow-through option to allow for "hands-off" observation of ESA-listed and other sensitive species.

In general, the invention can involve both devices and process steps for aquatic sampling of aquatic species and habitats. The invention can relate to a universal system that may be employed to achieve cross-species and cross-habitat sampling that can be comparable. Sampling can be accomplished in a manner that may have little or no impact on the organisms sampled, that may be cost-effective, and that may be applied broadly across varied species and habitats.

As can be appreciated from the above, the present invention disclosure includes a variety of aspects which may be selected in different combinations based upon the particular application or needs to be addressed. In a basic form, the invention can use a "push trawl" configuration mounted on a boat 110, perhaps a pontoon boat, with a concentrator net 100 and smaller drift net 102 attached to a net mouth opener brace 112 (which can be any means of holding a net mouth in an open position) at the front of the platform and to a sample chamber 108, perhaps a live well or live box, underneath the platform. Such a boat may be manned or unmanned, and may have an elementally resistant cabin on deck to protect an operator(s) or any equipment from the elements, perhaps wind, rain, and lightning, among others. A concentrator net 100 may have both a front end and a back end, and such a front end may be mounted to a net mouth opener brace 112 and such a back end may be mounted to a sample chamber 108. Such attachments may be rigid, and they may also be adjustable, perhaps even immediately responsive, such as to depth control(s) 114. A concentrator net 100 may serve to gradually funnel samples into a concentrated size for sampling, perhaps without substantial interruption of horizontal flow. Such a concentrator net 100 can even be a neutral vertical force concentrator net, perhaps applying substantially no vertical force to aquatic samples. A net mouth opener brace 112 may be mounted substantially at the fore of a boat (perhaps less than 20% of the total boat length aft of the bow) and may be vertically adjustable, including immediately adjustable, by a depth control 114, perhaps a winch, a piston, a gear drive, a worm drive, or a crane, and may have one or more wheels 116 or planar drags, perhaps skid plates, attached at the bottom in order to allow for sampling at various depths and across a variety of substrates. When present, a smaller drift net 102 may be mounted at its front end to the mouth of a concentrator net 100, and may serve to collect samples of plankton, microorganisms, and the like for separate purposes. Such a drift net 102 may in turn be attached at a back end to a tube 118 or any impermeable or semimpermeable means of transporting such samples to a sample chamber 108. A sample chamber 108, perhaps a live well or live box, can be organismically unrestrictive, perhaps allowing organisms to pass through with substantially no restrictions on their passage through such a chamber. Such a sample chamber 108 can even be an untactive sample chamber, which, if paired with an unemptied concentrator net, can perhaps allow for meaningful data collection without ever handling or touching aquatic samples directly. A sample chamber 108, perhaps a live well or live box, can be accessible from the platform, perhaps via a through-hull access hatch 120, and may be used for the collection and/or observation of fish and other aquatic organisms. The sample chamber 108, perhaps a live well or live box, may be adjustable in depth with relation to the bottom of the sampling platform via a depth control 114, perhaps a winch, a piston, a gear drive, a worm drive, or a crane, in order to allow for fish and other aquatic organisms to be directed to a sample chamber 108, perhaps a live well or live box, without becoming entangled in an attached concentrator net 100. A sample chamber 108, perhaps a live well or live box, may contain one or more capture net slots which may hold one or more variable mesh capture nets or screens in series, which may be immediately removable to allow for rapid sampling or to allow for aquatic organisms to transit the sample chamber 108, perhaps a live well or live box, and exit at the aft unimpeded. The sample chamber 108, perhaps a live well or live box, may also contain one or more video cameras 122, water sampling devices 104, and other sensors 124 may be continuously monitoring sensors and/or multienvironmental sensors, capable of continuously recording turbidity, temperature, dissolved oxygen, conductivity, chlorophyll level, phytoplankton level, nutrient level, total suspended solids, and other water quality data in a wide variety of environments, including, but not limited to, estuarine environments, shallow depth environments, tidal flats, deep channel environments, freshwater environments, saltwater environments, and the like. Such a sensor can also be a multidepth aquatic environment continuous monitoring sensor, perhaps capable of continuous monitoring before, after, or even during an adjustment in sampling depth. A genetic material sampling system(s), perhaps a noninvasive genetic material sampling system(s), including but not limited to an electronic DNA sampling system(s), may be present among such sensors, and may perhaps be integrated into a sample chamber 108. Such sensors 130 may be integrated with instruments 124 mounted outside of the sample chamber 108, perhaps a live well or live box, including but not limited to a fish finder, depth finder, GPS 132, and other mapping and/or timekeeping devices, perhaps a clock, in such a manner that all physical measurements, video images, and water samples can be automatically stamped with time and location information. A sample chamber 108 may include both biological and physical sensors capable of integrating their outputs, perhaps serving thereby as an integrated biological-physical sample chamber.

A general object of the invention is to provide a universal sampling system that can be utilized in varied habitats and that is not limited to only certain types of species. In keeping with this goal, it is an object to provide a system that can also be used in shallow and more challenging environments as well as more easily accessed environments.

Another goal is to provide a sampling system where data can be comparable across species and across habitats and so to provide an analysis and data capture possibility where different species and habitat sampling can be easily compared.

Yet another goal of embodiments of the invention can be to provide the possibility of sampling with reduced, little, or even no disturbance of the species being studied. In keeping with this goal, it is an object to provide a system that can be utilized in a manner that meets regulatory requirements for sensitive species and may even avoid any contact with the species for hands-off sampling.

The present invention can allow for sampling across both shallow and deep habitats using a single platform which can sample across multiple depths with improved efficiency and habitat sampling capabilities.

One of the broad objects of embodiments of the invention may be to allow for a continuation of sampling when a change in water depth is encountered. Thus, a goal can be to provide an ability to adjust the depth of the nets used for sampling. To achieve this, a depth control 114, perhaps a winch, a piston, a gear drive, a worm drive, or a crane, may be designed for raising and lowering a net mouth opener brace 112 to which sampling elements such as a concentrator net 100 and smaller drift net 102 may be attached at the fore of the platform. This depth control 114 may use pistons, winches, gear drives, worm drives, or cranes to raise and lower a net mouth opener brace 112, such as by 12-15 feet below the sampling platform.

Another broad object of embodiments of the invention may be to deliver captured fish and other aquatic organisms to a sample chamber 108, perhaps a live well or live box, for collection and/or observation while preventing or minimizing injury or mortality during sampling. Thus, a goal of embodiments of the invention may be to prevent the entanglement of organisms which have entered a concentrator net 100 and are being directed to a sample chamber 108, perhaps a live well or live box, for collection or observation. To achieve this, a depth control 114, perhaps a piston, a winch, a gear drive, a worm drive, or a crane, may be designed for raising and lowering a sample chamber 108, perhaps a live well or live box, in relation to the bottom of the sampling platform so as to minimize the angle of incidence between the bottom of a concentrator net 100 and the organisms which have entered such a net. Another goal of embodiments of the invention may be to prevent the escapement of larval species, zooplankton, phytoplankton, and other small organisms once they have entered a smaller drift net 102 in order to successfully deliver them to a sample chamber 108, perhaps a live well or live box, for collection and/or observation. To achieve this, embodiments may include a tube 118 or other impermeable or semi-impermeable structure which may be attached to a smaller drift net 102, perhaps near a net mouth opener brace 112 and/or to the front of a sample chamber 108, perhaps a live well or live box, underneath the sampling platform.

Another broad object of embodiments of the invention may be to allow for the linking of biological data directly to various physical data at the time of sampling. Thus, a goal of embodiments of the invention may be to integrate multiple methods of physical and biological data collection simultaneously. To achieve this in one manner, a system may be designed to integrate various sensors 106 and sampling equipment 104 located both within a sample chamber 108, perhaps a live well or live box, where aquatic organisms can be collected and/or observed and attached to the sampling platform outside of a sample chamber 108, perhaps a live well or live box, and to do so in such a manner as to provide a unique timestamp which may be associated with each sampling event.

Yet another broad object of embodiments of the invention may be to minimize downtime during sampling operations. Thus, a goal of the invention can be to provide multiple methods for collection and/or observation of fish and other aquatic organisms while the sampling platform is underway. To achieve this in one manner, a system, such as a capture net slot, may be designed which includes a method for inserting a variable mesh capture net, perhaps an immediately retrievable variable mesh capture net, or screen at the rear of a sample chamber 108, perhaps a live well or live box, to capture organisms. A through-hull access hatch 120 may also facilitate access to a sample chamber 108, perhaps a live well or live box, such as for dip netting. The system may be designed to allow for collection of fish and other aquatic organisms by dip netting whether a sample chamber 108, perhaps a live well or live box, is directly attached to the bottom of the platform or has been lowered to some depth below the sampling platform. Also to achieve this goal in one manner, a system, such as one or more capture net slots, may be designed which enables one or more variable mesh capture nets or screens to be inserted and removed, perhaps immediately, individually and in series near the front of a sample chamber 108, such as a live well or live box, in order to allow for rapid, sequential sampling of aquatic organisms entering a sample chamber 108, perhaps a live well or live box. Finally, to achieve this goal in one manner, a system, such as a sample viewing chamber 134, perhaps with an accompanying camera 136, may be designed which allows for image acquisition of organisms which transit a sample chamber 108, perhaps a live well or live box, in a transparent tube 118 or other impermeable or semi-impermeable structure comprising a viewing chamber after entering through a smaller drift net 102 at the front of the sampling platform, and an additional system may be designed which allows for image acquisition of organisms transiting a sample chamber 108, perhaps a live well or live box, after entering through a concentrator net 100 at the front of the sampling platform.

Still another broad object of embodiments of the invention can be to allow sampling to continue in circumstances where current sampling methods cannot achieve regulatory compliance (e.g., when ESA-listed fish or other sensitive species are present in the sampling area). Thus, a goal of embodiments of the invention can be to allow sampling without direct handling of fish and other aquatic organisms. To achieve this in one manner, a system, such as one or more capture net slots, may be designed to enable the removal of variable mesh capture nets or screens from the front and rear of a sample chamber 108, perhaps a live well or live box, in order to allow aquatic organisms to pass through a sample chamber 108, such as a live well or live box, unimpeded. This system may be coupled with a sample viewing chamber 138, a camera 122 which may capture images of each organism as it passes through the chamber, and a post- or other processing procedure, which may include image recognition, spot pattern analysis, chromatoscale, or morphometric analysis, including but not limited to the use of a morphometer 126, which may use morphometric models to identify species and calculate size, weight, sex, and other characteristics in order to allow for data collection without direct handling.

The following descriptions and referenced drawings are for selected embodiments of the present invention. Naturally, changes may be made to the disclosed embodiments while still falling within the scope and spirit of the present invention and the patent granted to its inventors.

DETAILED DESCRIPTION OF THE PREFERRED EMBODIMENTS

As can be seen from the figures, the basic components of the present invention may be embodied in several different ways. The present invention includes a variety of aspects, which may be combined in different ways. The following descriptions are provided to list elements and describe some of the embodiments of the present invention. These elements are listed with initial embodiments, however it should be understood that they may be combined and varied in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Figure 1:
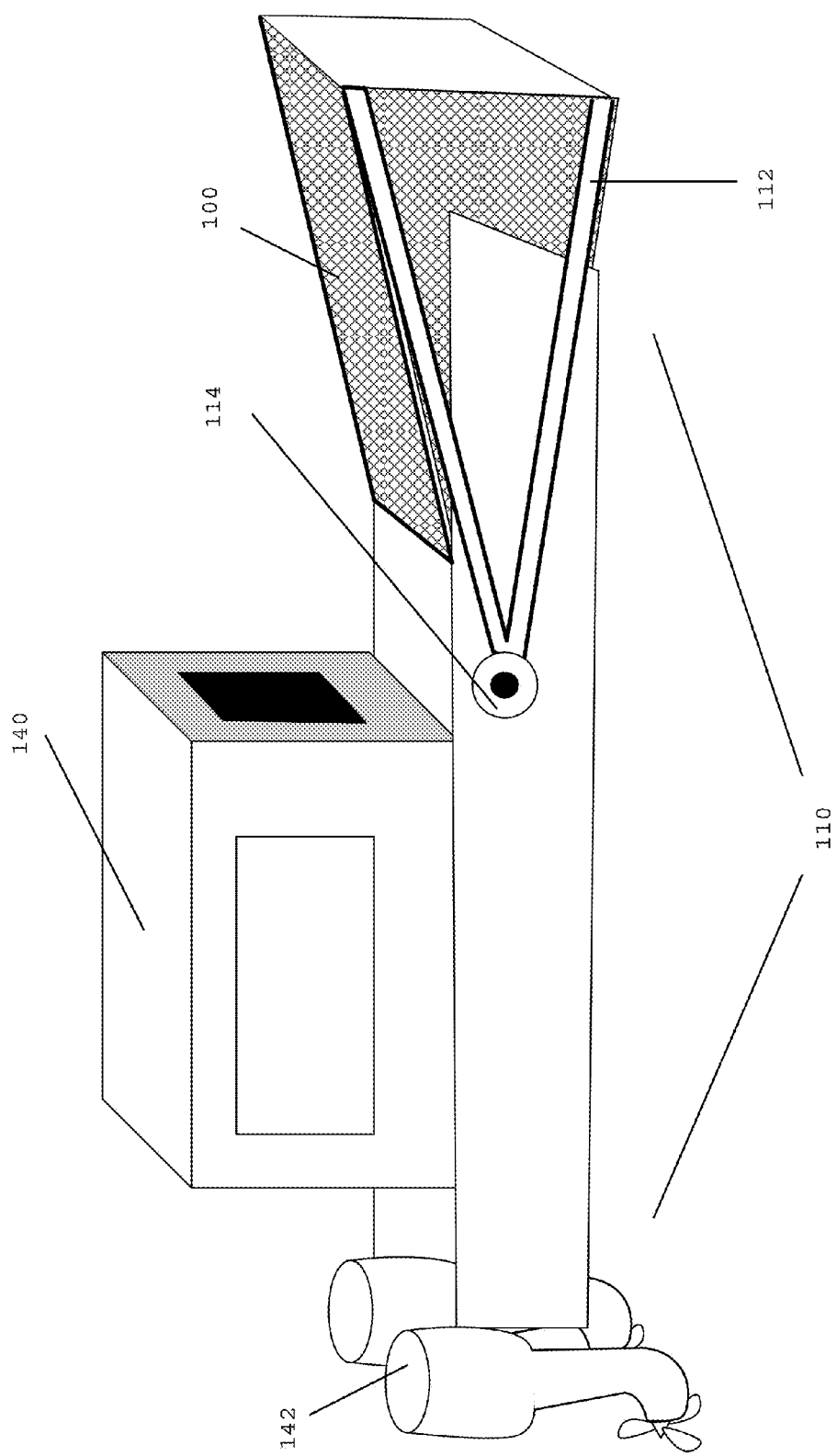
FIG. 1 is an image of a typical boat 110 with some of the basic components used to operate one embodiment of the invention drawn onto the picture, including a net mouth opener brace 112 for a concentrator net 100, and a depth control 114 for raising and lowering a net mouth opener brace 112.
Figure 2:
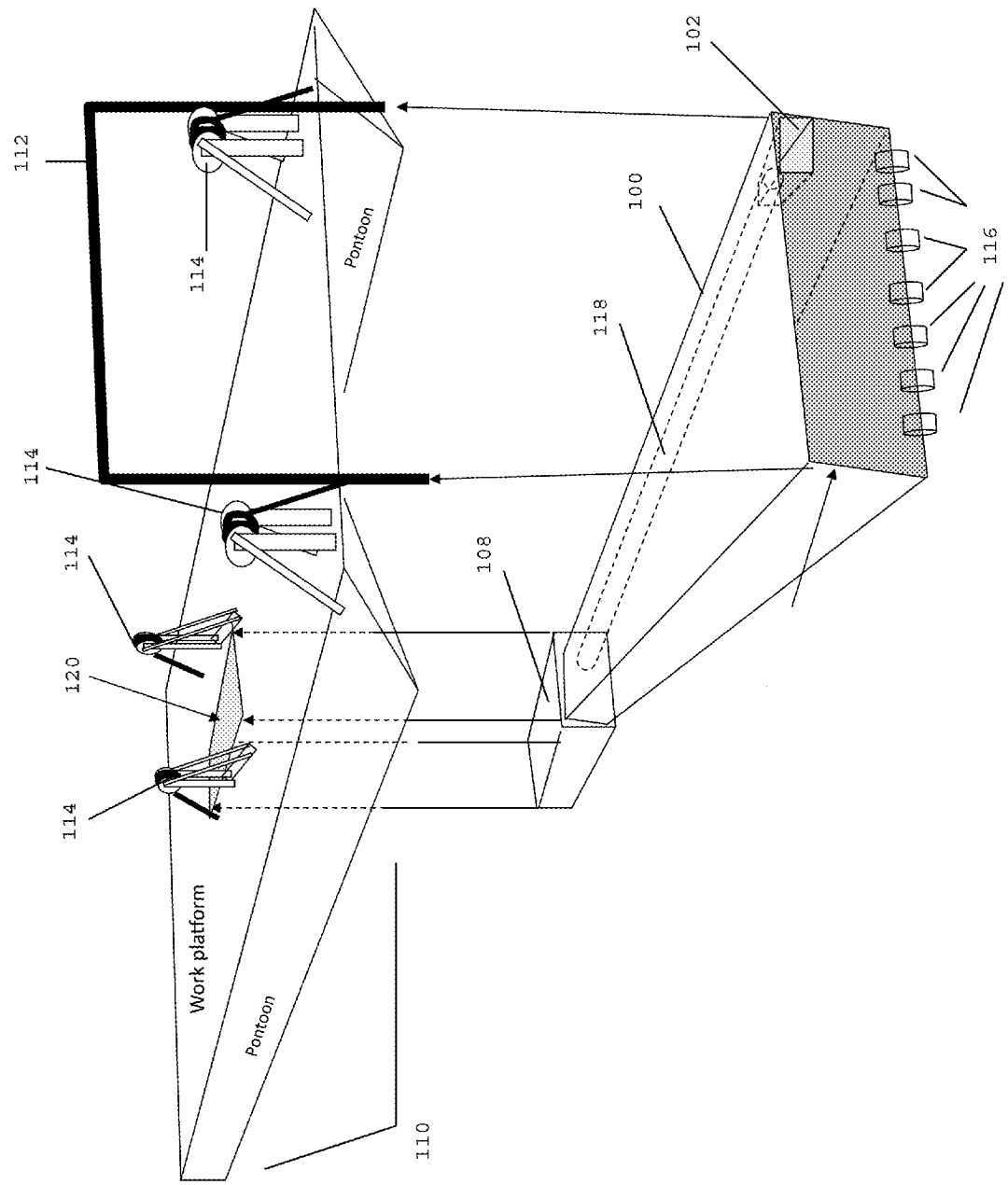
FIG. 2 is a drawing of one embodiment of the invention. The drawing shows that embodiments can include one or more depth controls 114 allowing for net mouth opener brace 112 and sample chamber 108 adjustment, a smaller drift net 102 installed within the mouth of the concentrator net 100, and one or more wheels 116 which allow the net mouth opener brace 112 to freely move over the bottom of the water body being sampled.
Figure 3:
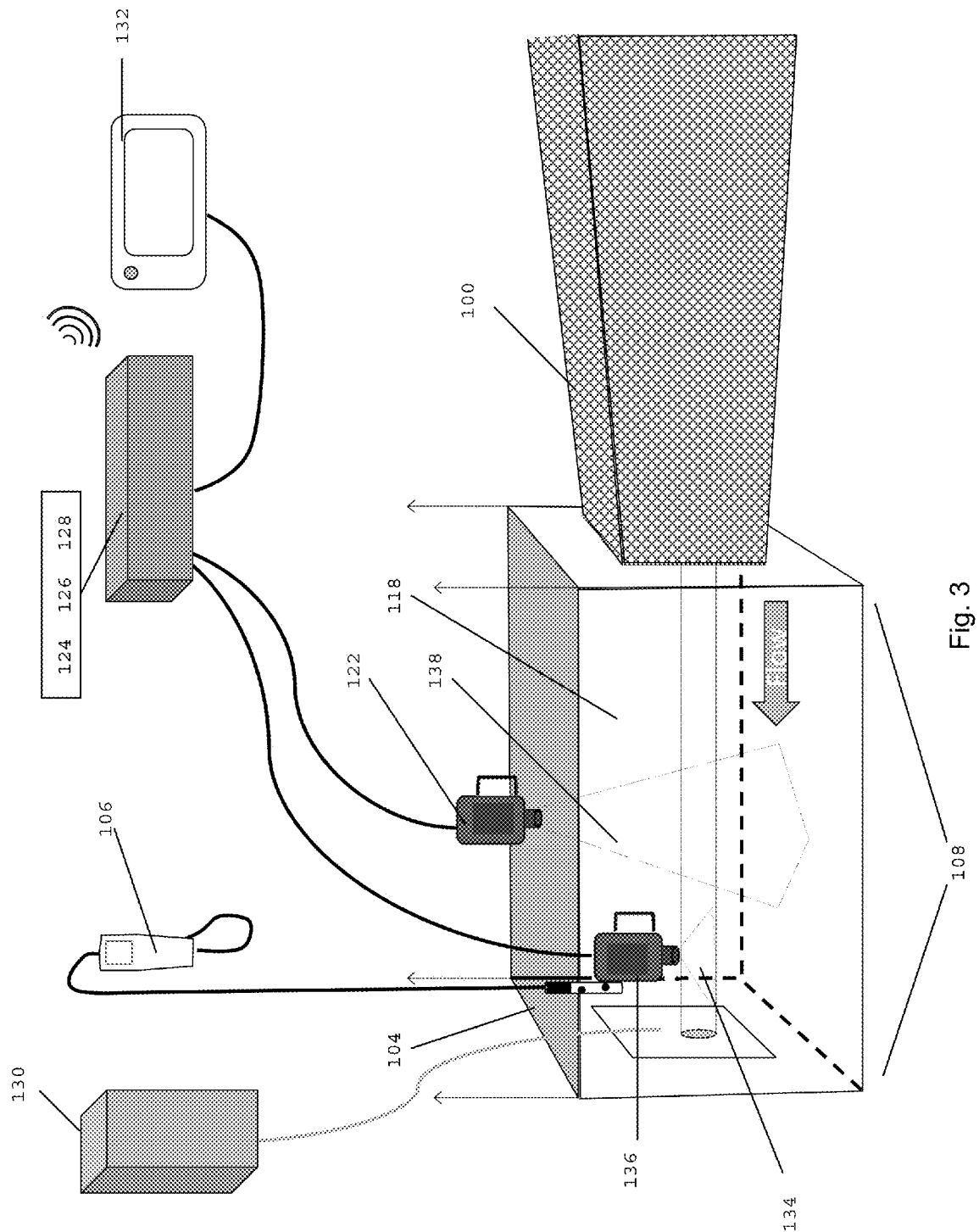
FIG. 3 is a drawing of a sample chamber 108 for one embodiment of the invention with some of the process elements shown. The drawing includes attachment of a concentrator net 100, a tube 118 carrying water to a sample chamber 108, the approximate location of a camera 122, representations of associated recording equipment 122 and other integrated devices 124, and arrows indicating the direction of water flow through the system.

FIGS. 1-2 illustrate different approaches of the present invention in both the design and operation of a net mouth opener brace 112 for one or more nets 100 among other aspects. FIG. 3 illustrate one embodiment of a sample chamber 108, perhaps a live well or live box, and associated equipment. In many of the embodiments of the present invention, the basic concept and components of the sampling system can remain the same. Components of embodiments may include (as representative non-limiting examples and possibilities): a boat 110, perhaps a pontoon boat, perhaps 24-36 feet in length, which may serve as the sampling platform; a retractable or removable canvas or such elementally resistant cabin 140, perhaps for protection of an operator(s) and equipment in inclement weather; one or more motors 142, perhaps an outboard motor, an inboard motor, a jet drive, or a trolling motor; a net mouth opener brace 112, perhaps at the fore of the platform, for one or more nets 100; one or more wheels 116, planar drags, perhaps skid plates, or the like attached to the bottom of a net mouth opener brace 112; a concentrator net 100; a smaller drift net 102; a tube 118 or other impermeable or semi-impermeable structure attached to the rear of a smaller drift net 102; a depth control 114 such as a crane, winch, gear drive, worm drive, or piston system for raising and lowering a net mouth opener brace 112 for one or more nets 100; a sample chamber 108, perhaps a live well or live box, perhaps with a capture net slot(s) at the aft or fore of a sample chamber 108, perhaps a live well or live box, for immediately retrievable variable mesh capture nets or screens, a transparent tube(s) 118 or other impermeable or semi-impermeable structure(s) which may include a sample viewing chamber(s) 134, an attached camera(s) 136, water sampling equipment 104 and one or more water quality sensors 106 (perhaps including temperature, dissolved oxygen, conductivity, chlorophyll level, phytoplankton level, nutrient level, total suspended solids, and turbidity meters), attachment brackets for a concentrator net 100, and an attachment port for a tube 118 or other impermeable or semi-impermeable structure attached to the rear of a smaller drift net 102; a frame attached to the rear of a concentrator net 100, perhaps inserted into brackets on a sample chamber 108, perhaps a live well or live box; a depth control 114, such as a winch, a gear drive, a worm drive, a crane, or a piston system for raising and lowering a sample chamber 108, perhaps a live well or live box; and one or more sensors 124, such as a velocimeter, fish finder, depth finder, GPS, camera, morphometer, chlorophyll sensor, phytoplankton sensor, nutrient sensor, total suspended solids sensor, video equipment, and/or other integrated devices as desired.

The following explains aspects of embodiments. It should be understood that these are examples of types of systems and configurations that can be used to achieve the broad aspects of the invention, and are not to be considered limiting as they are only examples of the many embodiments possible.

As shown in FIG. 1, embodiments of the invention can involve providing a net mouth opener brace 112 for the attachment of a concentrator net 100 mounted to the fore of a boat 110, such as a pontoon boat, perhaps 24-36 feet in length—perhaps in a "push trawl" design. A net mouth opener brace 112 can be adjusted vertically so as to adjust the depth of a concentrator net 100. FIG. 1 shows an embodiment of a net mouth opener brace 112, perhaps adjusted vertically by a depth control 114 such as a winch, a piston, a gear drive, a worm drive, or a crane. FIG. 2 shows another alternative embodiment of the net mouth opener brace 112, adjusted vertically by a depth control 114 such as a winch, a piston, a gear drive, a worm drive, or a crane or other system.

As shown in in FIGS. 2-3, embodiments of the invention may involve providing for a method to contain and direct fish and other aquatic organisms into an area in which they are accessible for sampling. In order to achieve this, a concentrator net 100 which may be attached on one end to a net mouth opener brace 112 (FIG. 2) and may be attached on the other end to an approximately rectangular or other appropriately shaped sample chamber 108, such as a live well or live box, perhaps by means of an iron frame or a frame constructed of another suitable rigid material, which may be configured to slide into a bracket or otherwise attach to the front of a sample chamber 108, perhaps a live well or live box. A smaller drift net 102 may be attached on one end, such as to a frame constructed of a rigid material, and may be attached in some manner to a net mouth opener brace 112 or a concentrator net 100. The other end of a smaller drift net 102 may be attached to a tube 118 or other impermeable or semi-impermeable structure which may be affixed to a sample chamber 108, perhaps a live well or live box, on its opposite end.

As shown in FIGS. 1 and 2, embodiments of the invention can include providing through-hull access, perhaps through a hatch 120, such as to sample chamber 108, perhaps a live well or live box, located underneath a boat 110, perhaps a pontoon boat. In some cases, it may be desirable to lower a sample chamber 108, such as a live well or live box, to some depth, perhaps up to 12-15 feet or more below the bottom of the sampling platform, in order to minimize entanglement of fish and other aquatic organisms in a concentrator net 100. FIG. 2 illustrates one embodiment of the present invention which provides for a depth control 114, such as a winch, a piston, a gear drive, a worm drive, a crane, or other system to raise and lower a sample chamber 108, such as a live well or live box. This may be combined with a mesh material or other flexible material attached to the sides of a sample chamber 108, such as a live well, and the bottom of the sampling platform in order to contain fish and other aquatic organisms within a sample chamber 108, such as a live well or live box.

As shown in FIG. 3, embodiments of the invention may involve providing for multiple methods to collect and/or observe fish or other aquatic organisms which enter the front of a perhaps approximately rectangular sample chamber 108, perhaps a live well or live box. The collection of organisms may be achieved by various methods. By incorporating a series of capture net slots at the fore of a sample chamber 108, such as a live well or live box, into which variable mesh capture nets or screens may be inserted to impede or capture fish and other aquatic organisms, collection can be facilitated. These variable mesh capture nets or screens may be immediately retrieved individually in order to alter or establish the appropriate collection of the organisms. Provision may also be made to prevent fish and other aquatic organisms from exiting a sample chamber 108, perhaps a live well or live box, when variable mesh capture nets or screens at the fore of a sample chamber 108 are not in place. This may be done by incorporating a variable mesh capture net or screen at the aft of a sample chamber 108. The incorporation of such a variable mesh capture net or screen, combined with flow through a sample chamber 108 from the fore to the aft (from right to left in FIG. 3) may contain fish and other aquatic organisms within a sample chamber 108, such as a live well or live box, for the purpose of allowing for collection by dip netting. Such a variable mesh capture net or screen may also be removable in order to allow for fish and other aquatic organisms to transit a sample chamber 108, such as a live well or live box, unimpeded for the purpose of observation and recordation without direct handling. Provision may be made to acquire images of organisms transiting a sample chamber 108, such as a live well or live box, by incorporating a transparent tube 118 or other impermeable or semi-impermeable structure, perhaps containing a sample viewing chamber 134 for organisms directed into a sample chamber 108, such as a live well or live box, such as by a smaller drift net 102. Images of these organisms may be acquired by a camera 136, perhaps mounted adjacent to a sample viewing chamber 134. Embodiments of the invention may also provide for a sample viewing chamber 138 and associated camera 122 for image acquisition of fish and other aquatic organisms directed into a sample chamber 108, such as a live well or live box, by a concentrator net 100. The present invention may also provide for an image post- or other processing procedure 128, such as spot pattern analysis, chromatoscale, image recognition, or morphometric analysis, including perhaps a morphometer 126, perhaps using such procedures to identify species and calculate size, weight, sex, and other characteristics.

Also as shown in FIG. 3, the invention may also involve providing for the integration of various devices in order to link biological and physical parameters for each sampling event. To achieve this, the sampling system may provide for hardware and software integration of one or more sensors 124, such as a velocimeter, fish finder, depth finder, GPS, other mapping devices and instruments, and video equipment mounted on the sampling platform with water quality sensors (perhaps including but not limited to temperature, dissolved oxygen, chlorophyll, phytoplankton, nutrient, total suspended solids, conductivity, and turbidity meters) mounted on the exterior or in the interior of a sample chamber 108 or elsewhere. Embodiments of the invention may integrate these devices and may allow for a unique timestamp and location information to be associated with each physical parameter measurement for each sampling event. In addition, embodiments of the invention may involve providing for a method to collect water samples associated with the collected and/or observed fish or other aquatic organisms. In order to achieve this, water sampling devices and/or equipment may be mounted in the interior or on the exterior of a sample chamber 108, such as a live well or live box, in such a manner as to enable collection of water samples, such as at the aft or in the interior of a sample chamber 108, such as a live well or live box, and/or an incorporated sample viewing chamber(s) 138. The devices and/or equipment may be integrated with other devices and sensors located on or in a sample chamber 108, such as a live well or live box, or mounted to the sampling platform in such a manner as to allow for a unique timestamp and location information to be associated with each sample for purposes of linking biological and physical parameters for each sampling event.

As should be appreciated, the various aspects of the embodiments described may be combined in different ways. Again, it is intended that the broad scope of this patent encompass all various permutations and combinations since each may be dependent on or selected for particular applications involved. The foregoing discussion describes the preferred embodiments of the present invention. It should be understood that changes may be made without departing from the essence of the invention. In this regard, it is intended that such changes would still fall within the scope of the patent. It simply is not practical to describe all possible revisions to the present invention which may be accomplished. To the extent any revision utilizes the essence of any one of the features of the present invention, it would naturally fall within the breadth of protection encompassed by this patent. Any changes or modifications made without departing from the broad aspects of the present invention are intended to be encompassed by this patent.

Again, different features were discussed for various aquatic sampling systems. The features of each of the aquatic sampling systems are not to be considered as applicable to only one aquatic sampling system but should be considered as useful for all of the presented aquatic sampling systems. Any of the mentioned integrated devices are examples and could change without distracting from the purpose of the integrated devices. While the invention has been described in connection with a preferred embodiment, it is not intended to limit the scope of the invention to the particular form set forth, but on the contrary, it is intended to cover such alternatives, modifications, and equivalents as may be included within the spirit and scope of the invention.

As can be easily understood from the foregoing, the basic concepts of the present invention may be embodied in a variety of ways. It involves both sampling techniques as well as devices to accomplish the appropriate sampling. In this application, the sampling techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that are or will be included in this or any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for this or any subsequent patent application. It should be understood that such language changes and broader or more detailed claiming may be accomplished at a later date (such as by any required deadline) or in the event the applicant subsequently seeks an additional patent filing(s) based on this filing. With this understanding, the reader should be aware that this disclosure is to be understood to support this or any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners.

Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sampler" should be understood to encompass disclosure of the act of "sampling"—whether explicitly discussed or not—and, conversely, were there effectively disclosure of the act of "sampling", such a disclosure should be understood to encompass disclosure of a "sampler" and even a "means for sampling." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any patents, publications, or other references mentioned in this application for patent are hereby incorporated by reference and can be relied upon as naming or depicting or disclosing elements that may be applicable to the present invention in its varied embodiments. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed below or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the sampling systems and devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in Hakim v. Cannon Avent Group, PLC, 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The invention claimed is:

1. A multiple aquatic environment sampling platform comprising:
   a boat;
   a net mouth opener brace mounted to said boat;
   a concentrator net comprising a front end and a back end, said front end adjustably attached to said net mouth opener brace;
   a depth control to which said concentrator net is responsive;
   a sample chamber to which said back end of said concentrator net is mounted;
   at least one multidepth aquatic environment continuous monitoring sensor; and
   a drift net comprising a front end and a back end, said front end of said drift net mounted to said front end of said concentrator net.

2. A multiple aquatic environment sampling platform as in claim 1, further comprising a sample viewing chamber.

3. A multiple aquatic environment sampling platform as in claim 2, further comprising a camera.

4. A multiple aquatic environment sampling platform as in claim 3, further comprising a morphometer.

5. A multiple aquatic environment sampling platform as in claim 1, wherein said at least one multidepth aquatic environment continuous monitoring sensor comprises at least one sensor selected from the group consisting of: a clock, a GPS module, a thermometer, a conductivity sensor, a depth finder, a pH sensor, a turbidity sensor, a velocimeter, a chlorophyll sensor, a phytoplankton sensor, a nutrient sensor, a total suspended solids sensor, and a dissolved oxygen sensor.

6. A multiple aquatic environment sampling platform as in claim 1, further comprising a tube to which said back end of said drift net is mounted.

7. A multiple aquatic environment sampling platform as in claim 6, wherein said tube comprises a tube connected to said sample chamber.

8. An aquatic sampling platform as in claim 1, further comprising a depth control to which said concentrator net is responsive.

9. An aquatic sampling platform as in claim 8, further comprising a depth control to which said sample chamber is responsive.

10. An aquatic sampling platform as in any of claims 8 and 9, wherein said depth control to which said concentrator net is responsive and said depth control to which said sample chamber is responsive comprise depth controls selected from the group consisting of: a winch, a piston, a gear drive, a worm drive, and a crane.

11. An aquatic sampling platform as in claim 1, wherein said sample chamber comprises a live well.

12. An aquatic sampling platform as in claim 1, wherein said sample chamber comprises an integrated physical-biological sample chamber.

13. An aquatic sampling platform as in claim 1, wherein said concentrator net comprises a neutral vertical force concentrator net.

* * * * *